(12) United States Patent
Cazzini

(10) Patent No.: US 8,444,585 B2
(45) Date of Patent: May 21, 2013

(54) CATHETER NEEDLE RETENTION AND PLACEMENT MONITORING SYSTEM AND METHOD

(75) Inventor: Karl H. Cazzini, Lindenhurst, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 659 days.

(21) Appl. No.: 12/696,850

(22) Filed: Jan. 29, 2010

(65) Prior Publication Data

US 2011/0190681 A1   Aug. 4, 2011

(51) Int. Cl.
   *A61M 25/02*   (2006.01)
(52) U.S. Cl.
   USPC .................. 604/4.01; 604/5.01; 604/6.16
(58) Field of Classification Search
   USPC .................. 604/4.01–11, 174, 180, 500, 540
   See application file for complete search history.

(56) References Cited

U.S. PATENT DOCUMENTS

| | | | |
|---|---|---|---|
| 4,966,590 A * | 10/1990 | Kalt | 604/180 |
| 4,976,698 A | 12/1990 | Stokley | |
| 5,036,859 A | 8/1991 | Brown | |
| 5,137,033 A | 8/1992 | Norton | |
| 5,266,928 A | 11/1993 | Johnson | |
| 5,557,263 A | 9/1996 | Fisher et al. | |
| 5,568,128 A | 10/1996 | Nair | |
| 5,570,026 A | 10/1996 | Buffaloe, IV et al. | |
| 5,790,036 A | 8/1998 | Fisher et al. | |
| 5,796,345 A | 8/1998 | Leventis et al. | |
| 5,868,723 A | 2/1999 | Al-Sabah | |
| 5,931,802 A | 8/1999 | Yoshida et al. | |
| 6,015,386 A | 1/2000 | Kensey et al. | |
| 6,038,914 A | 3/2000 | Carr et al. | |
| 6,090,048 A | 7/2000 | Hertz et al. | |
| 6,113,577 A | 9/2000 | Hakky et al. | |
| 6,189,388 B1 | 2/2001 | Cole et al. | |
| 6,193,519 B1 * | 2/2001 | Eggert et al. | 434/262 |
| 6,419,660 B1 * | 7/2002 | Russo | 604/180 |
| 6,979,306 B2 * | 12/2005 | Moll | 604/4.01 |

(Continued)

FOREIGN PATENT DOCUMENTS

| | | |
|---|---|---|
| DE | 102006041265 B3 | 12/2007 |
| EP | 1401518 | 3/2004 |

(Continued)

OTHER PUBLICATIONS

Written Opinion for International Application No. PCT/US2010/062396 dated Apr. 4, 2011.

(Continued)

*Primary Examiner* — Philip R Wiest
*Assistant Examiner* — Benjamin Klein
(74) *Attorney, Agent, or Firm* — K&L Gates LLP

(57) ABSTRACT

A blood access device includes (i) a first layer, a bottom surface of the first layer including (a) an adhesive or (b) a hook and loop material for securing the first layer to a patient, a first conductive attachment material located at a top surface of the first layer; (ii) a first conductor contacting the first conductive attachment material; (iii) a second layer, a second conductive attachment material located at a bottom surface of the second layer, the first and second conductive attachment materials configured to be releasably secured to each other; (iv) a second conductor contacting the second conductive attachment material; and (v) a blood vessel access member carried by the second layer.

20 Claims, 6 Drawing Sheets

U.S. PATENT DOCUMENTS

| | | | |
|---|---|---|---|
| 7,070,591 B2 | 7/2006 | Adams et al. | |
| 7,147,615 B2 | 12/2006 | Wariar et al. | |
| 7,176,344 B2 | 2/2007 | Gustafson et al. | |
| 7,276,041 B2 | 10/2007 | Moll | |
| 7,537,687 B2 | 5/2009 | Toyoda et al. | |
| 7,641,612 B1 | 1/2010 | McCall | |
| 7,670,289 B1 | 3/2010 | McCall | |
| 8,094,041 B2 * | 1/2012 | Wentland et al. | 340/945 |
| 2004/0116867 A1 | 6/2004 | Sternby | |
| 2005/0003825 A1 | 1/2005 | Miyake | |
| 2005/0010265 A1 | 1/2005 | Fassio et al. | |
| 2005/0256451 A1 | 11/2005 | Adams et al. | |
| 2006/0217669 A1 * | 9/2006 | Botha | 604/177 |
| 2007/0293748 A1 | 12/2007 | Engvall et al. | |
| 2008/0195060 A1 | 8/2008 | Roger et al. | |
| 2009/0082647 A1 | 3/2009 | Busby | |
| 2009/0118592 A1 | 5/2009 | Klitgaard | |
| 2009/0145446 A1 * | 6/2009 | DeDecker | 128/899 |
| 2009/0157000 A1 * | 6/2009 | Waller | 604/113 |
| 2009/0322543 A1 | 12/2009 | Crnkovich et al. | |
| 2010/0016809 A1 | 1/2010 | Grober et al. | |
| 2010/0100026 A1 | 4/2010 | Morris et al | |

FOREIGN PATENT DOCUMENTS

| | | |
|---|---|---|
| EP | 1892734 A1 | 2/2008 |
| WO | 96/25904 | 8/1996 |
| WO | 99/24145 | 5/1999 |
| WO | WO99/24145 A1 | 5/1999 |
| WO | 99/26686 | 6/1999 |
| WO | 99/29356 | 6/1999 |
| WO | 2006/001759 | 1/2006 |
| WO | 2009/024333 | 2/2009 |
| WO | 2009/075592 | 6/2009 |
| WO | 2009/109351 | 9/2009 |
| WO | 2009/112912 | 9/2009 |
| WO | 2009/112913 | 9/2009 |
| WO | 2010/040478 | 4/2010 |

OTHER PUBLICATIONS

Notification of Transmittal of the International Preliminary Report on Patentability for International Application No. PCT/US2010/062396 dated Jan. 30, 2012.

* cited by examiner

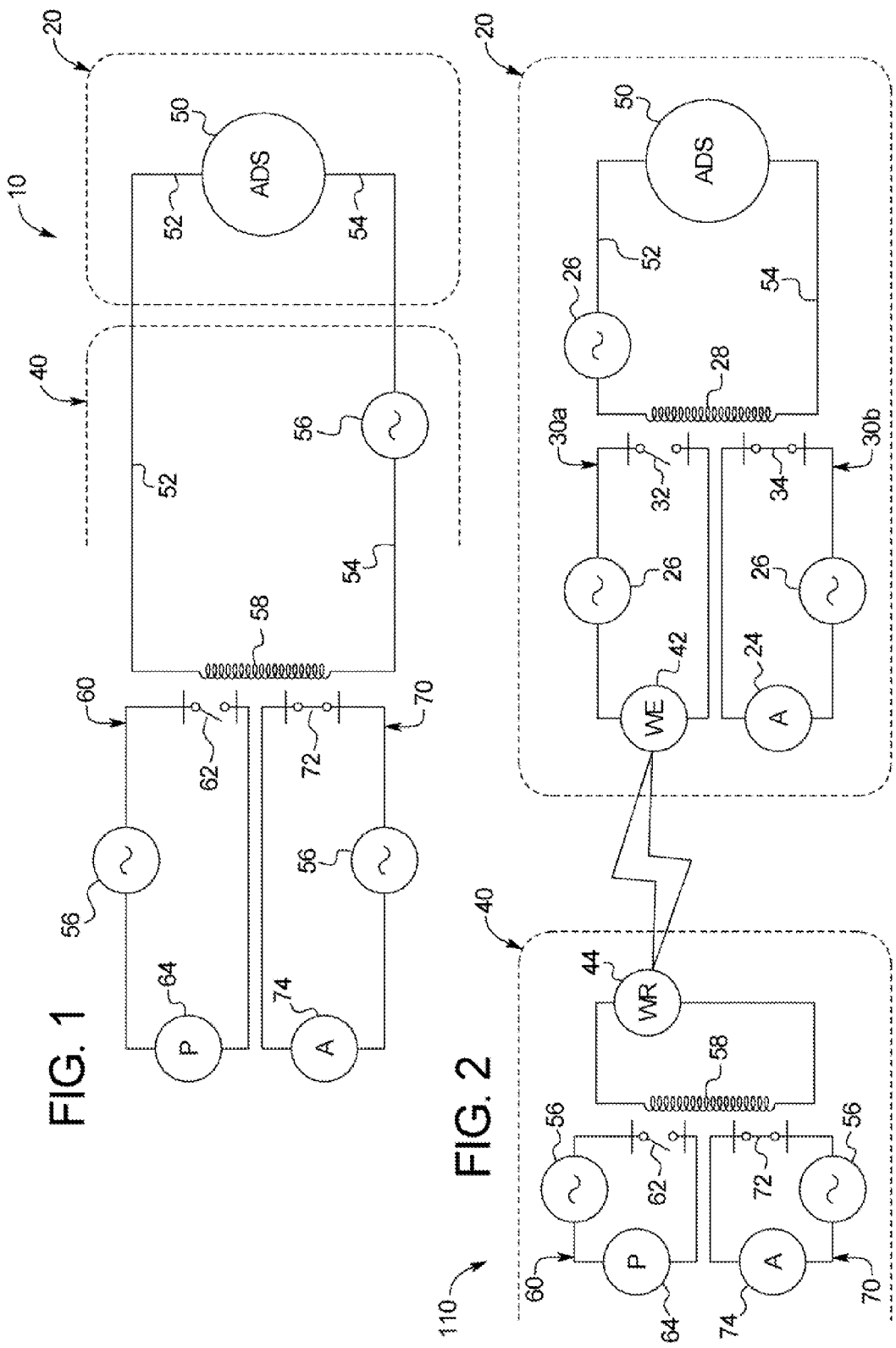

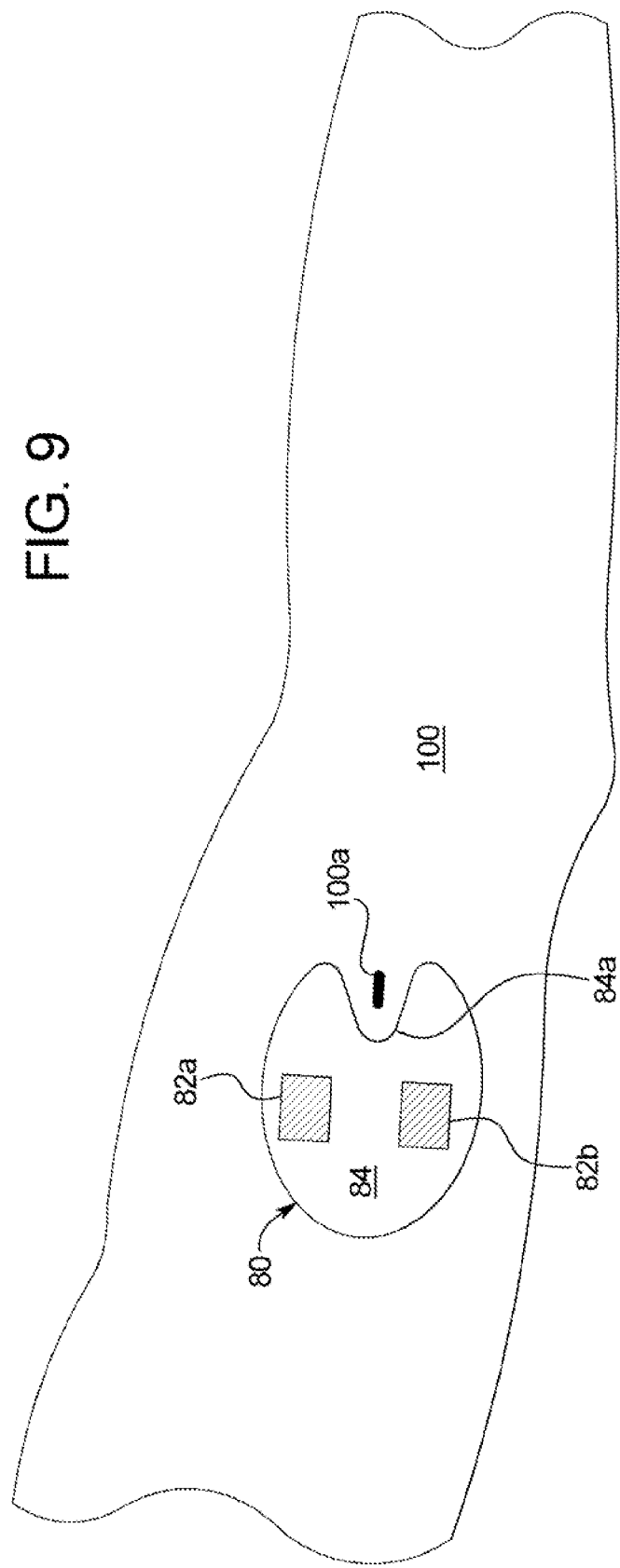

CATHETER NEEDLE RETENTION AND PLACEMENT MONITORING SYSTEM AND METHOD

BACKGROUND

The present disclosure relates to needle access disconnection detection.

It is especially important in instances in which a catheter enabled therapy is performed while the patient is sleeping or who otherwise may move in a manner likely to compromise catheter position and/or catheterization integrity to have an access disconnection detection system. Traditional means for attaching a catheter to a patient include the use of adhesive catheter securing devices, such as a Grip-Lok™ Universal Catheter Securement manufactured by Zefon International Inc. While a mechanical securement is beneficial, the device provides no recourse if the needle becomes dislodged despite the securement device.

Devices that sense when a needles dislodgement occurs are also available, such as a RedSense™ device manufactured by RedSense Medical, which alarms when an absorbent pad covering the catheterization site becomes saturated with blood flowing from a wound site upon inadvertent catheter withdrawal. Disadvantages of this device include its requirement of a relatively large amount of blood to activate the device, and the device's passive audible alarm, which may not be heard by patients with hearing impairment or subject to other environmental sound source. Also, the alarm is not fed back to the dialysis machine.

Other prior art access disconnection systems rely on current flowing through the patient's blood to indicate that a proper needle access exists. A drawback of these systems is that current must flow in many instances through high impedance or high resistance components, such as, a pump (membrane or peristaltic), a bubble trap, a valve or filter. These systems accordingly can succumb to noise, ground loops or loss of signal.

A more robust electrical access disconnection system, in particular for blood cleansing renal therapy treatments, such as hemodialysis, hemofiltration and hemodiatiltration, in which loss of a venous needle can lead to severe blood loss, is needed accordingly.

SUMMARY

The present disclosure sets forth multiple embodiments of an access disconnection system, e.g., for a hemodialysis ("HD"), hemofiltration ("HF") or hemodiafiltration ("HDF") system. It should be appreciated however that the concepts set forth herein are also applicable any blood access type of medical treatment and for intravenous, e.g., drug delivery systems and treatments.

The present disclosure sets forth an access disconnection detection system and method, which are capable of interfacing with the dialysis machine in the event of an access disconnection event to take corrective measures and sound an alarm if desired. The system and method, through the use of a conductive mechanical securement, such as that provided by conductive hook and loop retention members, can be configured in a geometry that allows for a detection of a change in the position of the catheter, without requiring the catheter to be completely withdrawn from the blood vessel. Further, the conductive hoop and loop members provide a securing force that exceeds the securing force enabled by known securement devices. The apparatus and method of the present disclosure therefore provided both a securement function and a feedback function.

Each of the embodiments discussed herein includes a first conductive attachment material and a second conductive attachment material. When the first and second conductive attachment materials are fastened to each other, a circuit is completed. The completion of the circuit is in one embodiment required for one or more component of the machine, such as a blood pump and/or a dialysate pump, to be operated. That is, a disconnection of the first and second conductive attachment materials breaks an electrical circuit, and if the blood pump and dialysate pump are running when such electrical breakage occurs, the blood pump or both the blood and dialysate pumps are stopped.

In a alternative embodiment, the electrical circuit powers a wireless emitter when made so that the wireless emitter sends a signal to a wireless receiver located at the medical fluid delivery, e.g., hemodialysis machine. The wireless receiver is in turn tied electrically or logically to the blood pump and possibly the dialysate pump, such that the signal needs to be received by the receiver for the one or more pump to be able to be operated. Again, if the signal is lost while the one or more pump is running, the one or more pump is stopped and the machine enters an alarm state.

In one embodiment, the first conductive attachment material is formed as part of a first layer, which attaches to the patient's body, e.g., arm. A bottom surface of the first layer can be provided accordingly with an adhesive or adhesive material. A top surface of the first layer (facing away from the patient's body) is provided accordingly with the first conductive attachment material. It is contemplated to provide an inflatable bladder between the adhesive material and the first conductive material to aid in releasing the adhesive from the patient's skin.

The second conductive attachment material is provided on the lower surface of a second layer. A needle, cannula or catheter (referred to herein collectively as a blood vessel access member or simply as a needle) can then be attached to the upper surface of the second layer. When the user inserts the needle into the patient's blood vessel, the first and second attachment materials come into registry with each other. The patient then presses the second layer and second conductive attachment material to the first layer and first conductive attachment material, which has been adhered to the patient's skin.

The mating of the first and second conductive attachment materials therefore not only provides an access disconnection feature; the mating also serves to prevent the needle from coming free from the patient's blood vessel in the first place. In an embodiment, the first and second conductive attachment materials are made of a conductive hook and loop material, which is commercially available. The hook and loop materials can be used interchangeably as the first or second conductive materials.

It is contemplated to allow the needle to be removeably attached to the second layer, e.g., via butterfly flanges extending from the needle, such that the needle can be disposable and made as cost effective as possible, while either one or both of the first and second layers can be reused. It is accordingly contemplated in an alternative embodiment to replace the adhesive with one or more releasably securable strap, wherein the strap can also be connected via a hook and loop material, so that the first layer can be used again and again without the fear of an adhesive becoming non-functional.

First and second conductors can be attached to the first and second attachment materials. The first or second conductors electrically connect the attachment materials to desired electrical components, such as a voltage source, a switch, and/or a wireless emitter. In an alternative electrical arrangement, the first and second conductor attachment materials are provided as part of a resistive bridge circuit which increases the sensibility of the system.

The attachment materials can further alternatively be provided in a matching pattern on the first and second layers to allow the needle to be inserted into the patient's blood vessel without the attachment materials interfering with such insertion. For example, the second attachment material can be provided on the underside of butterfly flanges that are originally folded up along a housing of the needle. Upon insertion, the butterfly flanges are folded down to meet a matching pattern of first conductive attachment material positions provided on portions of the first layer. The conductors are structured to run to each of the mated portions or patches of the pattern, such that the sensitivity of the access disconnection sensing is increased, that is, any of the mated pattern portions coming unsecured breaks the pumping circuit and causes the machine to enter an alarm state.

It is accordingly an advantage of the present disclosure to provide a needle access disconnection system that does not require electrical connection to the patient's blood.

It is another advantage of the present disclosure to provide a needle access disconnection system that fails safe.

It is another advantage of the present disclosure to provide a needle access disconnection system that enables a disposable, relatively inexpensive patient blood vessel access member to be used.

It is yet another advantage of the present disclosure to provide a needle access disconnection system that is robust, cost effective and sensitive.

It is still a further advantage of the present disclosure to provide a needle access disconnection system that is configurable to operate with a medical fluid machine in a wired arrangement or wirelessly.

It is yet a further advantage of the present disclosure to provide a needle access disconnection system that provides both needle securement and needle dislodgment feedback.

Additional features and advantages are described herein, and will be apparent from the following Detailed Description and the figures

BRIEF DESCRIPTION OF THE FIGURES

FIG. 1 is a system schematic for a wired embodiment of the blood access system and method of the present disclosure.

FIG. 2 is a system schematic for a wireless embodiment of the blood access system and method of the present disclosure.

FIG. 9 is a top plan view of another embodiment of the blood access device of the present disclosure, which additionally forms a guide for needle insertion.

DETAILED DESCRIPTION

Figure 3:
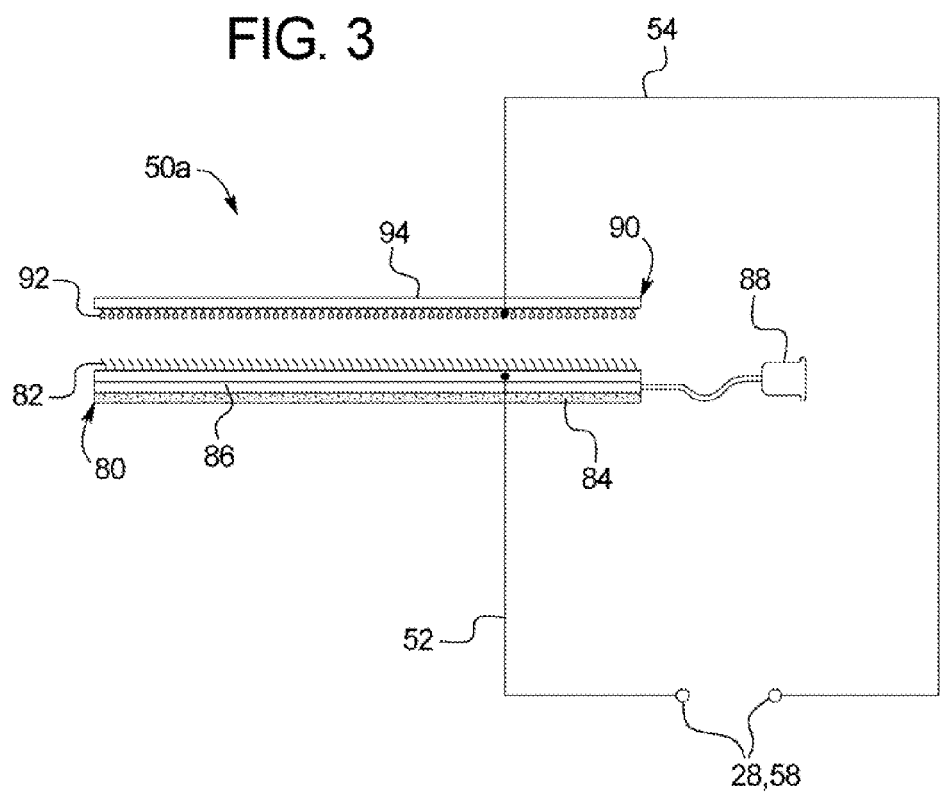
FIG. 3 is a side elevation view of one embodiment of the blood access system and method of the present disclosure.

Referring now to the drawings and in particular to FIG. 1, one embodiment of a blood access device and corresponding system and method is illustrated by system 10. System 10 includes a blood access device 20, which is generally shown in bordered phantom line. System 10 also includes a medical machine 40, such as a hemodialysis ("HD") machine, hemofiltration ("HF") machine, hemodialfiltration ("HDF") machine, continuous renal replacement therapy ("CRRT") machine, drug infusion pump or other type of medical device that involves the accessing of the patient's blood vessel with a needle, cannula, catheter or other type of blood vessel access member (which may be referred to herein collectively simply as a needle). In one preferred embodiment, medical machine 40 is an HD machine, and in particular a hemodialysis machine set forth in published U.S. Patent Publication 2009/0101549, the entire contents of which are incorporated herein by reference and relied upon.

Blood access device 20 includes an access disconnection apparatus 50, which is described in detail below beginning at FIG. 3. Access disconnection apparatus 50 communicates with conductors, wires or leads 52 and 54, which extend from blood access device 20 to medical fluid delivery machine 40. Conductors 52 and 54 can for example be printed circuit board traces or wires located on a printed circuit board ("PCB") of blood access device 20. PCB traces 52 and 54 can then communicate via a protected cable with medical fluid delivery machine 40.

In an alternative embodiment, conductors 52 and 54 extend along or within the medical delivery tubing that delivers a medical fluid from machine 40 to the patient at blood access device 20. In an HD, HDF or HF embodiment, there is a small section of tubing that extends from each of the arterial and venous needles inserted into the patient. Those small sections of tubing are then connected to arterial and venous lines running from the HD, HF or HDF machine 40, e.g., via standard lure lock connectors. It is contemplated to extend the wire through both, the short tubings extending from the needles or catheters and the arterial and venous lines of machine 40. Various embodiments for extending a wire along the outside or within the wall of arterial and venous tubings are disclosed in U.S. patent application Ser. No. 12/360,503, filed Jan. 27, 2009, entitled "Sealant Applicator With Malleable Section", assigned to the assignee of the present disclosure, the entire contents of which are incorporated herein by reference. In any case, conductors 52 and 54 in an embodiment extend all the way to machine 40 in one embodiment of system 10.

In the illustrated embodiment, a voltage source 56 is provided along one of conductors 52 and 54 to supply power to blood access device 20 from within machine 40. Voltage source 56 can be an AC or DC voltage source as desired. Conductors 52 and 54 terminate at a logic coil 58. Coil 58 can be the coil of an electromechanical relay or of a solid-state relay, such as one provided within a programmable logic controller ("PLC"), which is used commonly with electrically controlled devices for the control of electrical logic.

Relay coil 58 in the illustrated embodiment is configured to energize or change the state of a normally open electrical contact 62 associated with a pump circuit 60, and a normally closed contact 72 associated with an alarm circuit 70. Each of pimp circuit 60 and alarm circuit 70 is powered by a power supply or voltage source 56, which can be the same or different voltage source 56 used in the circuit of conductors 52 and 54. It should be appreciated that circuits 60 and 70 have been simplified and may contain other electrical components known to those skilled in the art.

In operation, access disconnection apparatus 50 is normally not conducting. When the patient inserts the needle into the patient's blood vessel, current flows through conductors 52 and 54 and energizes logic coil 58. The energization of logic coil 58 causes contacts 62 and 72 to change state. In circuit 60, normally open contact 62 closes, such that voltage supply 56 can selectively supply power to pump 64, causing the pump to operate. Likewise, the energization of logic coil 58 causes normally closed contact 72 to open, such that current no longer is supplied from voltage source 56 to alarm 74.

Alarm 74 can be a visual alarm, audio alarm or audiovisual alarm. For example, alarm 74 may simply be a light that is lit prior to the patient inserting the needles of conductors 52 and 54 into the patient's blood vessel. After such insertion, coil 58 becomes energized, opens contact 72 and causes the light of alarm 74 to switch off. In this state, that is, when blood access or patient access has been made, it is contemplated for system 10 to convert alarm 74 into a more intrusive audio or audio visual alarm, such that if one of the needles comes loose from the patient, coil 58 becomes de-energized, contact 72 reverts to its non-energized or closed state and voltage supply 56 powers the more intrusive alarm 74, which alerts the patient (who may for example be sleeping) to promptly correct the access disconnection situation.

Circuitry 60 may have additional override circuitry (not illustrated) that allows pump 64 to be operated even though coil 58 has not been energized. For purposes of the present disclosure, however, circuit 60 when coil 58 is in an unenergized state, maintains contact 62 in its normally open condition, such that voltage supply 56 cannot supply power to pump 64. When access disconnection apparatus 50 is in a blood vessel properly accessed condition, coil 58 is energized and normally open contact 62 changes to its energized or closed state, which enables voltage source 56 to selectively power pump 64. Thereafter, if a needle disconnection event occurs, coil 58 is no longer energized and contact 62 reverts to its unenergized or open state, and causes pump 64 to stop.

While system 10 is shown having both circuitry 60 and circuitry 70, it may be desirable in certain instances to provide only one of pump circuitry 60 or alarm circuitry 70.

Referring now to FIG. 2, an alternative wireless system 110 is illustrated. System 110 includes many of the same components described above for system 10, including machine voltage source 56 and pump and alarm circuits 60 and 70 respectively, which operate as described above for system 10, including any additional desirable electrical components common to those of skill in the art, which are not shown here for ease of illustration. Also, just like with system 10, normally open contact 62 and normally closed contact 72 are energized via logic coil 58, located within machine 40. Blood access device 20 includes access disconnection apparatus 50 and conductors 52 and 54 as described above for system 10.

In system 110, however, blood access device 20 is not powered by machine 40 and instead includes its own separate voltage supply 26, which can be a single voltage supply for all components of blood access device 20 or can be multiple, e.g., regulated, voltage supplies for different components of blood access device 20. In an embodiment, voltage supply 26 is a rechargeable battery supply, for which it is contemplated to configure alarm circuitry 30b to sound an alarm 24 whenever the voltage level stored in supply 26 falls below a preset level.

Blood access device 20 includes pump energizing and alarm output circuits 30a and 30b, which operate in a similar manner to pump and alarm output circuits 60 and 70 described above for system 10. In particular, when the needle is not accessing the patient's blood vessel, no current flows from voltage source 26 through coil 28, such that coil 28 remains unenergized. Consequently, normally open contact 32 of pump energize or wireless emitter circuit 30a and normally closed contact 34 of alarm circuit 30b remain in their unenergized states. This condition results in an alarm being posted at alarm 24, which can again be a dual-stage type of alarm that merely shines a light to inform the patient prior to insertion of the needle, but that changes into a more invasive alarm upon an access disconnection event. In the unenergized state, power supply 26 does not supply power to a wireless emitter 42 coupled to wireless emitter circuit 30a, such that no signal is sent wirelessly to a wireless receiver 44 located in an electrical circuit with coil 58 within machine 40. When the patient has accessed a blood vessel, current is enabled to flow through coil 28, causing contacts 32 and 34 to switch to their energized states. Here, alarm circuit 30b disables alarm 24, while wireless emitter circuit 30a becomes energized such that wireless emitter 42 sends a wireless signal to wireless receiver 44.

Upon receiving wireless signal at receiver 44, coil 58 becomes energized and enables pump 64 to be operated and causes alarm 74 to become disabled as described above (including all alternative embodiments) for system 10. Wireless emitter 42 and wireless receiver 44 communicate in an embodiment via a known wireless communication protocol, such as Bluetooth™ Zigbee™, or other protocol, e.g., one based on IEEE 802.

Figure 4:
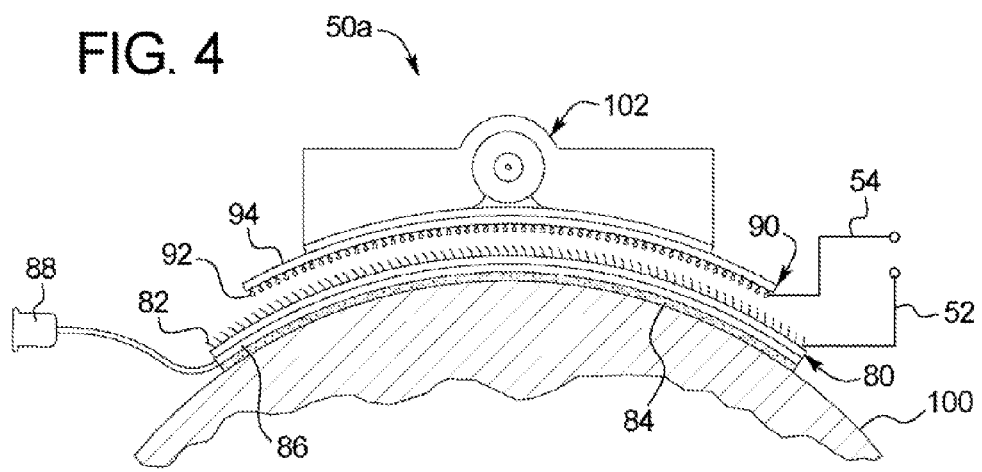
FIG. 4 is a side elevation view of one embodiment of FIG. 3 attached to a patient.
Figure 5:
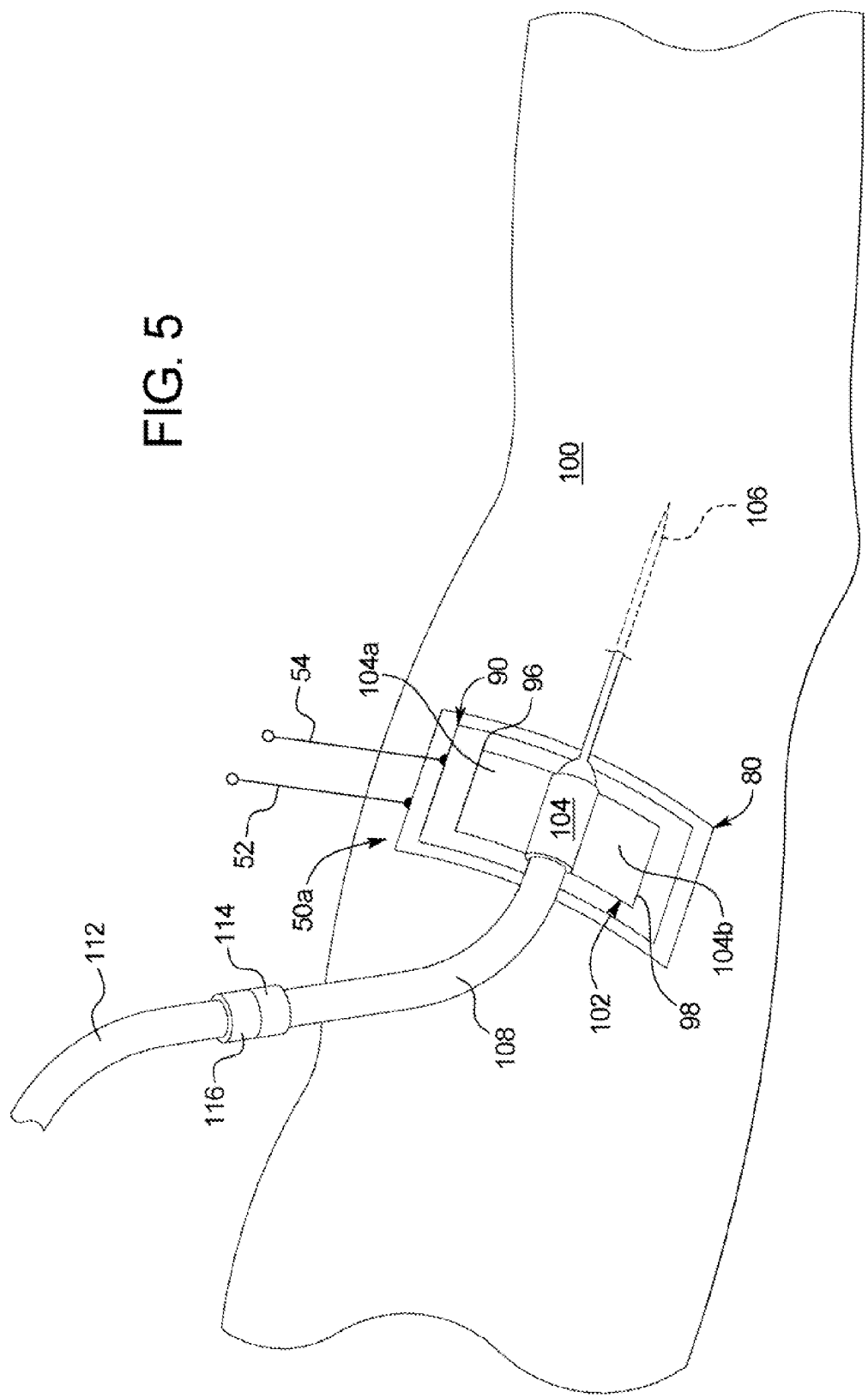
FIG. 5 is a top plan view of one embodiment of FIG. 3 attached to a patient.

Referring now to FIGS. 3 to 5, one embodiment of access disconnection apparatus 50 (referring collectively to each of the access disconnection apparatuses 50a, 50b, 50n discussed herein) is illustrated by access disconnection apparatus 50a. Access disconnection apparatus 50 is illustrated in operation with a single needle, e.g., the venous needle and blood line. Alternatively, apparatus 50 may be reconfigured to operate with both venous and arterial needles.

As discussed above, access disconnection apparatus 50a includes conductors or leads 52 and 54, which extend to logic coil 28 for wireless system 110 or to logic coil 58 for hardwired system 10. Access disconnection apparatus 50a includes a first layer 80 and a second layer 90. First layer 80 includes on its upper surface a first conductive attachment material 82. On its lower surface, layer 80 includes an adhesive or adhesive layer 84. As illustrated in FIG. 4, adhesive layer or adhesive 84 bonds lower layer 80 to skin 100 of the patient, such as to the patient's arm.

In the illustrated embodiment, an inflatable bladder 86 is provided between first conductive attachment material 82 and the adhesive or the adhesive layer 84. A syringe port 88 communicates fluidly with inflatable bladder 86 to enable the patient to insert a syringe (not illustrated) into syringe port 88 in an air-tight or liquid-tight manner to inject air or a liquid, respectively, into inflatable bladder 86 to inflate the bladder. The purpose of inflatable bladder is to help the patient remove the adhesively attached lower layer 80 from the patient's skin when it is needed. In an alternative embodiment, inflatable bladder 86 and corresponding syringe port 88 are not provided.

Upper layer 90 of access disconnection apparatus 50a includes a second conductive attachment material 92, which may be produced with or laminated to an upper surface 94. Conductive material 92 is configured to be releasably secured to conductive material 82, so as to releasably attach upper layer 90 to lower layer 80. In the illustrated embodiment, conductive material 82 is a conductive hook material, which attaches releasably to a conductive loop material 92 of upper layer 90. In an alternative embodiment, a conductive loop material is provided as the first conductive material 82 of lower layer 80, while the conductive hook material is provided as the second conductive attachment material 92 of second or upper substrate 90. One suitable embodiment of a conductive hook and loop material is commercially available from Less EMF Inc., 809 Madison Ave., Albany, N.Y., 12208 USA (1-518-432-1550).

As seen in FIGS. 3 and 4, conductor 52 is connected electrically to first conductive attachment material 82, while conductor 54 is attached electrically to second conductive material 92. It should therefore be appreciated that the releasable attachment of second conductive material 92 to first conductive material 82 completes an electrical circuit, which then has the effects described above in connection with systems 10 and 110. In one embodiment, conductors 52 and 54 are secured to layers 80 and 90, respectively, by laminating the conductors between the conductive attachment material and an adjacent layer. Alternatively, conductors 52 and 54 can be mechanically and/or adhesively bonded to conductive materials 82 and 92.

FIGS. 4 and 5 illustrate that the blood vessel access member or needle 102 is secured to upper surface 94 of upper layer 90. In one preferred embodiment, at least one of layers 80 and 90 is reusable. It is therefore contemplated to releasably attach needle 102 to upper surface 94. That is, as seen in FIG. 5, blood vessel access device 102 in one embodiment includes a housing 104 with a needle or cannula 106 that extends from housing 104. FIG. 5 shows piercing member 106 of needle 102 inserted into patient 100, where it accesses the patient's blood vessel. A small section of tubing 108 is provided with needle 102. Small tubing section 108 is connected to arterial or venous line 112 via a connector 114 of tubing 108 that mates sealingly and releasably to a mating connector 116 of arterial or venous line 112.

To ensure that the patient is not infected by the medical treatment of systems 10 and 110, it is contemplated to produce needle 102a a disposable, one use, item, which is packaged and then sterilized. It is accordingly desirable to produce needle 102 as safe but as cost effective as possible. It is contemplated to therefore structure upper conducting layer 90 so that it can be reused along with lower conducting layer 80, and to construct upper layer 90 so as to secure releasably to needle 102. To this end, upper conducting layer 90 can be provided with slits 96 and 98 that accept butterfly flanges 104a and 104b to secure needle 102 releasably to upper layer 90 prior to the conductive attachment of upper layer 90 to lower conductive layer 80.

If it is found that adhesive layer 84 of lower conducting layer 80 is not readily reusable, lower layer 84 can alternatively be extended such that it wraps around the patient's arm. Here, lower layer 84 is provided with, for example, a reusable mating hook and loop material instead of the adhesive layer. In this manner, lower layer 84 of lower conducting layer 80 can be releasably and reusably wrapped around the patient's arm. First conductive attachment material 82 extends upwards away from patient's skin 100. The patient inserts piercing member 106 of needle 102 into the patient's blood vessel and concurrently or thereafter secures the blood access by attaching upper conductive material 92 to lower conductive material 82, which also completes an electrical circuit for the various purposes discussed above.

Figure 6:
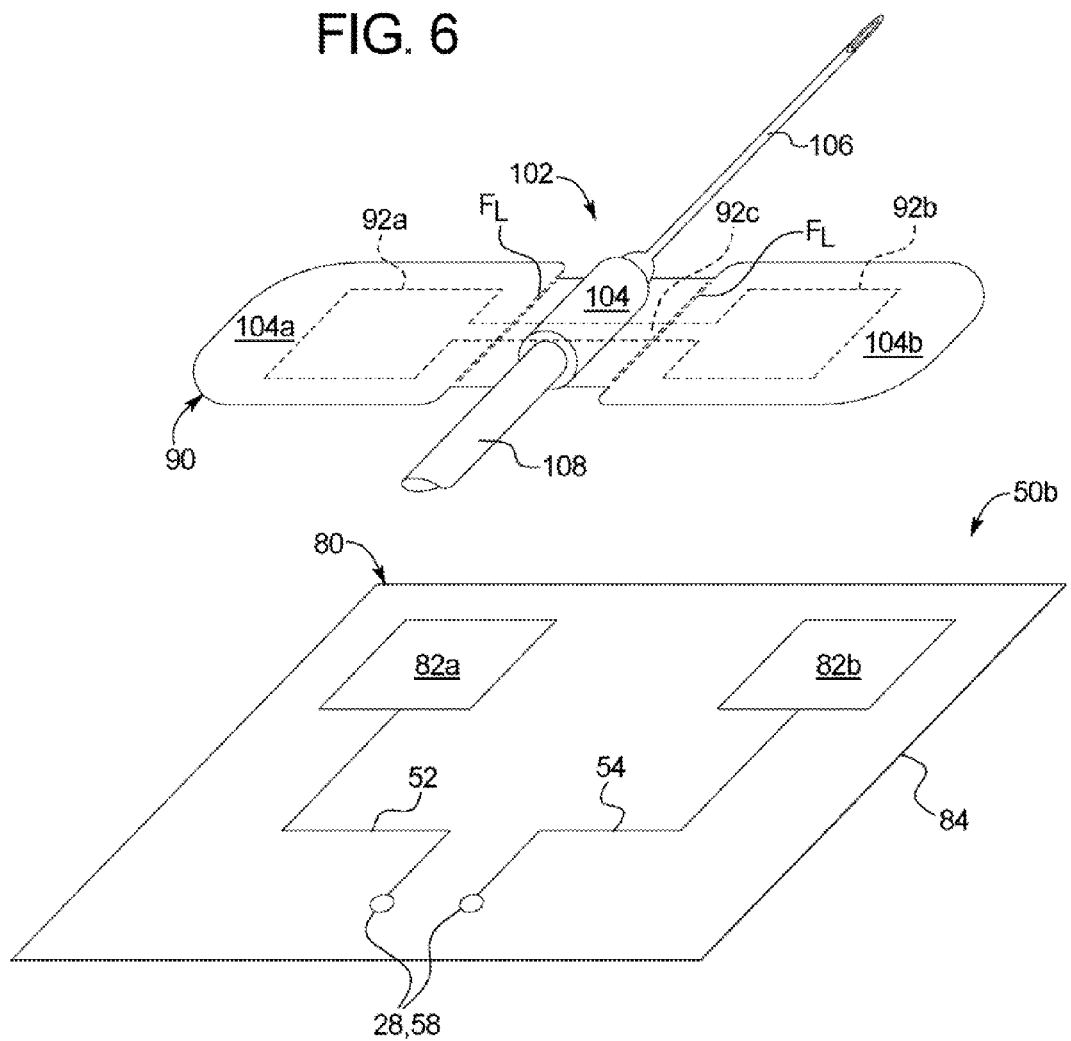
FIG. 6 is a perspective view of another embodiment of the blood access system and method of the present disclosure.

Referring now to FIG. 6, an alternative access disconnection apparatus 50b is illustrated. Access disconnection apparatus 50b includes a lower layer 80 like above, which attaches to skin 100 of the patient. As before, lower layer 84 can be provided with an adhesive or adhesive material that attaches lower layer 80 to the patient's skin 100. Alternatively, lower material 84 is configured to extend around the patient's arm and attach to itself releasably via, e.g., a hook and loop material.

Upper conducting layer 90 of access disconnection apparatus 50b is incorporated into housing 104 of needle 102. Here, second conductive attachment material is provided in two portions 92a and 92b, which are connected together electrically via a conducting strip of the material 92c. Portions 92a and 92b and strip 92c are shown in phantom line because in the perspective view of FIG. 6 the portions and strip are located beneath butterfly flanges 104a and 104b of needle housing 104. As discussed above, needle 102 in an embodiment is provided with a short section of tubing 108 that releasably secures to one of the arterial and venous lines extending from machine 40.

Lower conducting layer 80 is provided accordingly with mating first conductive attachment material portions 82a and 82b. As illustrated in FIG. 6, conductive attachment portion 92a secures releasably to conductive attachment material portion 82a, while conductive attachment portion 92b secures releasably to lower conductive attachment material portion 82b. In the alternative access disconnection apparatus 50b, both conductors 52 and 54 are provided with lower conducting layer 80 and extend to one of the logic coils 28 or 58 discussed and illustrated above.

Access disconnection apparatus 50b is advantageous in one respect because butterfly flanges 104a and 104b fold upwards along fold lines FL shown in FIG. 6. When flanges 104a and 104b are folded upwards, the patient can slide the central portion of the butterfly flanges of housing 104 along a smooth patch of lower material 84 when inserting piercing member 106 of needle 102 into the patient's blood vessel. When blood access is achieved, the patient then folds butterfly flanges 104a and 104b downwardly along fold lines FL to cause conducting portion 92a to secure releasably to conducting portion 82a and conducting portion 92b to secure releasably to conducting portion 82b. It is contemplated to size portions 82a, 82b, 92a and 92b to allow for a slight or even moderate misalignment between the upper and lower mating portions, while still allowing the portions to mate in a secure and electrically conductive manner.

In one embodiment, conductors 52 and 54 are provided as conductive traces or conductive links that extend to the electrical components, such as a voltage source 26, alarm 24, control coil 28 and/or wireless emitter 42. Conductive traces 52 and 54 are then covered with a protective electrically insulating layer, such as an electrically insulating plastic sheet or film.

Figure 7:
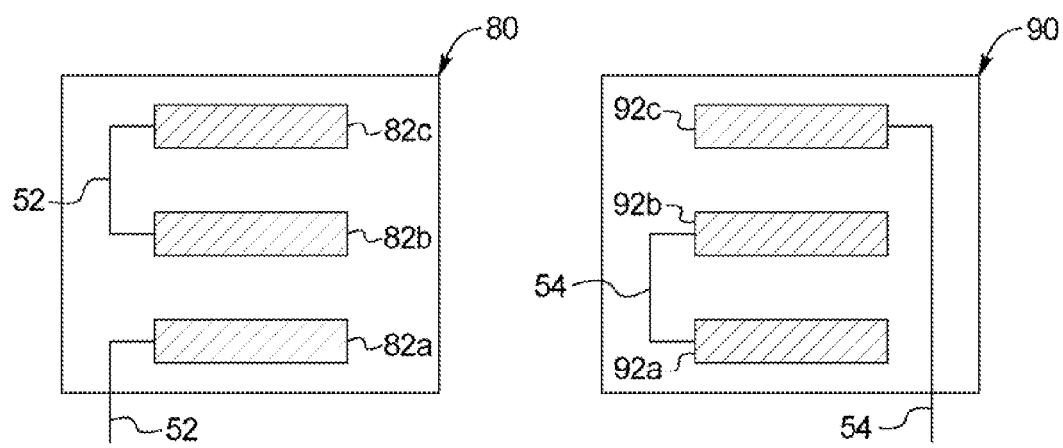
FIG. 7 is a plan view of one embodiment of the present disclosure having a pattern of conductive material portions.

Referring now to FIG. 7, in another alternative embodiment the conductive attachment portions are provided in an array format and are connected electrically in series with conductors 52 and 54. If any of the mating conductor portions come free or unattached from each other, the electrical circuit is broken and the responsive measures discussed above with systems 10 and 110 are undertaken. In the example illustrated in FIG. 7, lower conducting layer 80 includes three portions 82a, 82b and 82c made of the first conductive attachment material. Upper conductive layer 90 includes three mating portions 92a, 92b and 92c made of the second conductive attachment material.

Conductors 52 and 54 are connected in one embodiment to portions 82a, 82b and 82c and 92a, 92b and 92c, respectively, such that current must flow as illustrated (i) from conductor 52 through conductive portion 82a, (ii) through conductive portion 92a, (iii) through conductor 54, (iv) through conductive portion 92b, (v) through conductive portion 82b, (vi) through a second segment of conductor 52, (vii) through conductive portion 82c, (viii) through conductive portion 92c, and (ix) out a second segment of conductor 54. It should be appreciated that if any of the mating pairs 82a/92a, 82b/92b or 82c/92c of the conductive attachment portions comes free from one another, the electrical circuit is broken. The embodiment of FIG. 7 accordingly enhances (a) resolution of the position of needle 102 and (b) connection integrity.

The embodiment of FIG. 7 may be used as an access disconnection device for both venous and arterial needles and blood lines. For example, portion pair 82a/92a may be associated with the venous needle, while portion pair 82c/92c is associated with the arterial needle. A disconnection or partial disconnection of either needle opens the circuit. Third portion pair 82b/92b could be structured then to provide additional sensitivity to both the venous and arterial access disconnection detectors.

Figure 8:
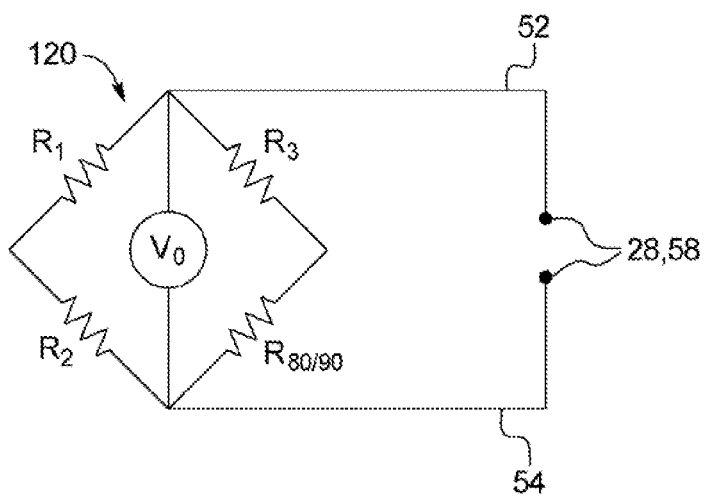
FIG. 8 is a schematic electrical view of the blood access device of the present disclosure, which is configured with an electrical resistance bridge circuit.

Referring now to FIG. 8, it is also contemplated to arrange conductive segments 82a, 82b, 82c, 92a, 92b, or 92c, such that they make-up one or more arm of, e.g., a resistance bridge circuit 120, which also enhances electrical sensitivity to incursions of the catheter or cannula 106 from a normal access position. In circuit 120, resistance $R_{80/90}$ is an unknown resistance of the conductive loop and velcro layers 80 and 90 (referring collectively to each of the embodiments described herein including those of conductive segments 82a, 82b, 82c, 92a, 92b, or 92c), wherein the resistance is related to the common surface area between layers 80 and 90. It is contemplated to locate circuit 120 within a microchip locally at blood access device 20 and to structure resistance $R_{80/90}$ as a varying digital potentiometer.

Resistors $R_1$, $R_2$ and $R_3$ are resistors of known resistance, with the resistance of $R_2$ being adjustable via the microchip. As is known in the art, if the ratio of the two resistances in the "known leg" ($R_2/R_1$) is equal to the ratio of the resistances in the "unknown leg" ($R_{80/90}/R_3$), then the voltage between points 122 and 124 will be zero, such that no current can flow through the voltage output meter $V_0$. Upon the user's application of layer 90 to layer 80, the microchip varies $R_2$ until the zero voltage, zero current condition is reached. Because the resistances of resistors $R_1$, $R_2$ and $R_3$ can be known to a high precision, the resistance of $R_{80/90}$ can be measured to a high precision, such that very small changes in $R_{80/90}$ disrupt the balance and are readily detected at the microchip. Also, advantageously, a voltage reading for when the disconnection devices are properly engaged is reset for each application to zero.

Referring now to FIG. 9, an alternative embodiment for lower conductive layer 80 is illustrated. Lower conductive layer 80 includes skin mounting material 84, which can be adhesive or can be provided alternatively with a hook and loop fastener around patient's arm 100, as discussed above. Skin attachment material 84 includes a "V"-shaped or "U"-shaped notch 84a that extends around an intended or desired needle insertion site 100a of the patient's arm 100. "V"-shaped or "U"-shaped notch 84a enables the access disconnection apparatuses 50 of the present disclosure to provide an additional advantageous function, namely, focusing and aiding the patient in accessing a vein or artery at a desired location.

Aspects of the subject matter described herein may be useful alone or in combination one or more other aspect described herein. Without limiting the foregoing description, in a first aspect of the present disclosure, a blood access device includes: a first layer, a bottom surface of the first layer including (i) an adhesive or (ii) a hook and loop material for securing the first layer to a patient, a first conductive attachment material located at a top surface of the first layer; a first conductor contacting the first conductive attachment material; a second layer, a second conductive attachment material located at a bottom surface of the second layer, the first and second conductive attachment materials configured to be releasably secured to each other; a second conductor contacting the second conductive attachment material; and a blood vessel access member carried by the second layer.

In accordance with a second aspect of the present disclosure, which may be used in combination with the first aspect, the blood vessel access member is a needle, catheter or cannula.

In accordance with a third aspect of the present disclosure, which may be used in combination with any one or more of the preceding aspects, the first and second conductors are configured to extend to and interface with a blood therapy treatment machine.

In accordance with a fourth aspect of the present disclosure, which may be used in combination with any one or more of the preceding aspects, the blood vessel access member is attached along a top surface of the second layer.

In accordance with a fifth aspect of the present disclosure, which may be used in combination with any one or more of the preceding aspects, the first conductive attachment material is one of a hook and a loop material and the second conductive attachment material is one of a loop and a hook material, respectively.

In accordance with a sixth aspect of the present disclosure, which may be used in combination with any one or more of the preceding aspects, the first and second conductive attachment materials form matching patterns.

In accordance with a seventh aspect of the present disclosure, which may be used in combination with the sixth aspect, the first conductor contacts each segment of the first conductive attachment material pattern and the second conductor contacts each segment of the second conductive attachment material pattern.

In accordance with an eighth aspect of the present disclosure, which may be used in combination with any one or more of the preceding aspects, the first layer defines a guide for guiding the blood vessel access member to a desired access site for accessing the blood vessel.

In accordance with a ninth aspect of the present disclosure, which may be used in combination with any one or more of the preceding aspects, the first layer includes an inflatable bladder located between the adhesive, when provided, and the first conductive attachment material.

In accordance with a tenth aspect of the present disclosure, which may be used in combination with any one or more of the preceding aspects, the second layer is configured to enable the blood vessel access member to access the blood vessel prior to an attachment of the first conductive attachment material to the second conductive attachment material.

In accordance with an eleventh aspect of the present disclosure, which may be used in combination with any one or more of the preceding aspects, the blood access device includes first and second butterfly flanges extending from a housing holding the blood vessel access member, the second conductive attachment material distributed onto the first and second butterfly flanges.

In accordance with a twelfth aspect of the present disclosure, which may be used in combination with the eleventh aspect, the first and second butterfly flanges are configured to be deployed to allow the second conductive attachment material to be secured to the first conductive attachment material after the blood vessel access member has accessed the blood vessel.

In accordance with a thirteenth aspect of the present disclosure, which may be used in combination with any one or more of the preceding aspects, at least one of the first and second layers is reusable.

In accordance with a fourteenth aspect of the present disclosure, which may be used in combination with any one or more of the preceding aspects, at least one function of the dialysis machine is disabled if the second conductive attachment material comes loose from the first conductive attachment material.

In accordance with a fifteenth aspect of the present disclosure, which may be used in combination with any one or more of the preceding aspects, the blood access device includes a signal emitter in electrical communication with the first and second conductors, the signal emitter emitting or changing a signal to a medical device having a signal receiver when the second conductive attachment material is attached to or unattached from the first conductive attachment material.

In accordance with a sixteenth aspect of the present disclosure, which may be used in combination with any one or more of the preceding aspects, a blood therapy system includes: a blood pump; a blood access device configured to access a blood vessel of a patient, the blood access device including (i) a first conductive attachment material for connection to the patient, (ii) a first conductor contacting the first conductive attachment material, (iii) a second conductive attachment material, and (iv) a second conductor contacting the second conductive attachment material; and wherein the blood pump enabled for operation when second conductive attachment material is connected to the first conductive attachment material.

In accordance with a seventeenth aspect of the present disclosure, which may be used in combination with any one or more of the preceding aspects and aspect sixteen, the blood therapy system includes an electrical supply in electrical communication with the first and second conductors.

In accordance with an eighteenth aspect of the present disclosure, which may be used in combination with any one or more of the preceding aspects and aspect sixteen, the blood therapy system is a dialysis system, and which includes a blood vessel access member carried with the second conductive attachment material, the blood vessel access member configured to access the blood vessel of the patient.

In accordance with a nineteenth aspect of the present disclosure, which may be used in combination with any one or more of the preceding aspects and aspect sixteen, the first conductive attachment material is one of a hook and a loop material and the second conductive attachment material is one of a loop and a hook material, respectively.

In accordance with a twentieth aspect of the present disclosure, which may be used in combination with any one or more of the preceding aspects and aspect sixteen, the first and second conductive attachment materials form part of a resistance bridge circuit used for enabling or disabling the blood pump.

In accordance with a twenty-first aspect of the present disclosure, which may be used in combination with any one or more of the preceding aspects, a blood therapy system includes: a machine including a blood pump; and a blood access device configured to access a blood vessel of a patient, the blood access device including (i) a first conductive attachment material for connection to the patient, (ii) a first conductor contacting the first conductive attachment material, (iii) a second conductive attachment material, (iv) a second conductor contacting the second conductive attachment material, and (v) a signal emitter in electrical communication with the first and second conductors, the signal emitter emitting a signal to a signal receiver located with the machine to enable operation of the blood pump when the second conductor attachment material is connected to the first conductor attachment material.

In accordance with a twenty-second aspect of the present disclosure, any of the structure and functionality illustrated and described in connection with FIG. 1 may be used in combination with any one or more of the preceding aspects.

In accordance with a twenty-third aspect of the present disclosure, any of the structure and functionality illustrated and described in connection with FIG. 2 may be used in combination with any one or more of the preceding aspects.

In accordance with a twenty-fourth aspect of the present disclosure, any of the structure and functionality illustrated and described in connection with FIG. 3 may be used in combination with any one or more of the preceding aspects.

In accordance with a twenty-fifth aspect of the present disclosure, any of the structure and functionality illustrated and described in connection with FIG. 4 may be used in combination with any one or more of the preceding aspects.

In accordance with a twenty-sixth aspect of the present disclosure, any of the structure and functionality illustrated and described in connection with FIG. 5 may be used in combination with any one or more of the preceding aspects.

In accordance with a twenty-seventh aspect of the present disclosure, any of the structure and functionality illustrated and described in connection with FIG. 6 may be used in combination with any one or more of the preceding aspects.

In accordance with a twenty-eighth aspect of the present disclosure, any of the structure and functionality illustrated and described in connection with FIG. 7 may be used in combination with any one or more of the preceding aspects.

In accordance with a twenty-ninth aspect of the present disclosure, any of the structure and functionality illustrated and described in connection with FIG. 8 may be used in combination with any one or more of the preceding aspects.

In accordance with a thirtieth aspect of the present disclosure, any of the structure and functionality illustrated and described in connection with FIG. 9 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A blood access device comprising:
   a first layer, a bottom surface of the first layer including (i) an adhesive or (ii) a hook and loop material for securing the first layer to a patient, a first conductive attachment material located at a top surface of the first layer;
   a first conductor contacting the first conductive attachment material;
   a second layer, a second conductive attachment material located at a bottom surface of the second layer, the first and second conductive attachment materials configured to be releasably secured to each other;
   a second conductor contacting the second conductive attachment material; and
   a blood vessel access member carried by the second layer, wherein the first conductive attachment material includes one of a hook and a loop material and the second conductive attachment material includes one of a hook and a loop material, respectively.

2. The blood access device of claim 1, wherein the first and second conductors are configured to extend to and interface with a blood therapy treatment machine.

3. The blood access device of claim 1, wherein the blood vessel access member is attached along a top surface of the second layer.

4. The blood access device of claim 1, wherein the blood vessel access member includes a housing releasably secured to the second layer.

5. The blood access device of claim 1, wherein the first and second conductive attachment materials form matching patterns.

6. The blood access device of claim 5, wherein the first conductor contacts each segment of the first conductive attachment material pattern and the second conductor contacts each segment of the second conductive attachment material pattern.

7. The blood access device of claim 1, wherein the first layer defines a guide for guiding the blood vessel access member to a desired access site for accessing the blood vessel.

8. The blood access device of claim 1, wherein the first layer includes an inflatable bladder located between the adhesive, when provided, and the first conductive attachment material.

9. The blood access device of claim 1, wherein the second layer is configured to enable the blood vessel access member to access the blood vessel prior to a securement of the first conductive attachment material to the second conductive attachment material.

10. The blood access device of claim 1, which includes first and second butterfly flanges extending from a housing holding the blood vessel access member, the second conductive attachment material distributed onto the first and second butterfly flanges.

11. The blood access device of claim 10, wherein the first and second butterfly flanges are configured to be deployed to allow the second conductive attachment material to be secured to the first conductive attachment material after the blood vessel access member has accessed the blood vessel.

12. The blood access device of claim 1, wherein at least one of the first and second layers is reusable.

13. A system including a dialysis machine in electrical communication with the blood access device of claim 1, wherein at least one function of the dialysis machine is disabled if the second conductive attachment material comes loose from the first conductive attachment material.

14. The blood access device of claim 1, which includes a signal emitter in electrical communication with the first and second conductors, the signal emitter emitting or changing a signal to a medical device having a signal receiver when the second conductive attachment material is attached to or unattached from the first conductive attachment material.

15. A blood therapy system comprising:
a blood pump;
a blood access device configured to access a blood vessel of a patient, the blood access device including (i) a first conductive attachment material for connection to the patient, (ii) a first conductor contacting the first conductive attachment material, (iii) a second conductive attachment material, and (iv) a second conductor contacting the second conductive attachment material; and
wherein the blood pump is enabled for operation when second conductive attachment material is connected to the first conductive attachment material, and
wherein the first conductive attachment material includes one of a hook and a loop material and the second conductive attachment material includes one of a hook and a loop material, respectively.

16. The blood therapy system of claim 15, which includes an electrical supply in electrical communication with the first and second conductors.

17. The blood therapy system of claim 15, which is a dialysis system, and which includes a blood vessel access member carried with the second conductive attachment material, the blood vessel access member configured to access the blood vessel of the patient.

18. The blood therapy system of claim 15, wherein the blood vessel access member includes a housing releasably secured to the second layer.

19. The blood therapy system of claim 15, wherein the first and second conductive attachment materials form part of a resistance bridge circuit used for enabling or disabling the blood pump.

20. A blood therapy system comprising:
a machine including a blood pump; and
a blood access device configured to access a blood vessel of a patient, the blood access device including (i) a first conductive attachment material for connection to the patient, (ii) a first conductor contacting the first conductive attachment material, (iii) a second conductive attachment material, (iv) a second conductor contacting the second conductive attachment material, and (v) a signal emitter in electrical communication with the first and second conductors, the signal emitter emitting a signal to a signal receiver located with the machine to enable operation of the blood pump when the second conductor attachment material is connected to the first conductive attachment material, and
wherein the first conductive attachment material includes one of a hook and a loop material and the second conductive attachment material includes one of a hook and a loop material, respectively.

* * * * *